United States Patent [19]
Muller et al.

[11] Patent Number: 5,928,185
[45] Date of Patent: Jul. 27, 1999

[54] IONTOPHORESIS DEVICE FOR THE TRANSCUTANEOUS DELIVERY OF AN ACTIVE PRINCIPLE SUCH AS AN ANIONIC OLIGOSACCHARIDE

[75] Inventors: Daniel Muller, Pau; Alain Barbier, Saint-Clement-de-Riviere; Henry Saunal, Montpellier, all of France

[73] Assignees: Sanofi; Elf Aquitaine, both of France; Akzo Nobel N.V., Netherlands

[21] Appl. No.: 08/875,106

[22] PCT Filed: Jan. 24, 1996

[86] PCT No.: PCT/FR96/00114

§ 371 Date: Sep. 29, 1997

§ 102(e) Date: Sep. 29, 1997

[87] PCT Pub. No.: WO96/22808

PCT Pub. Date: Aug. 1, 1996

[30] Foreign Application Priority Data

Jan. 24, 1995 [FR] France .................................. 95 00757

[51] Int. Cl.6 ....................................................... A61N 1/30
[52] U.S. Cl. .............................................................. 604/20
[58] Field of Search .......................... 604/20, 289, 304; 607/115

[56] References Cited

U.S. PATENT DOCUMENTS

| | | | |
|---|---|---|---|
| 4,841,041 | 6/1989 | van Boeckel et al. | 536/118 |
| 5,068,226 | 11/1991 | Weinshenker et al. | 514/58 |
| 5,320,597 | 6/1994 | Sage, Jr. et al. | 604/20 |
| 5,320,731 | 6/1994 | Muller et al. | 204/299 |

*Primary Examiner*—Manual Mendez
*Attorney, Agent, or Firm*—Bacon & Thomas, PLLC

[57] ABSTRACT

A device comprising a reversible negative electrode in contact with a reservoir element containing an electrolyte which contains an active principle such as an anionic oligosaccharide, particularly a pentasaccharide, in at least partially ionised form, a positive electrode alone or in combination with an electrolyte-containing receptacle, and an electrical signal generator connectable to both electrodes. The generator is arranged to apply electrical signals between the electrodes, which signals have an average voltage such that the average current density generated between the electrodes is 0.05–0.25 mA/cm$^2$. The amount of active principle in the reservoir element combined with the negative electrode is 0.5–12 mg per cm$^2$. The amount of active principle in the reservoir element combined with the negative electrode is 0.5–12 mg per cm$^2$ and per mAh of current through 1 cm$^2$ of the electrode.

19 Claims, 1 Drawing Sheet

IONTOPHORESIS DEVICE FOR THE TRANSCUTANEOUS DELIVERY OF AN ACTIVE PRINCIPLE SUCH AS AN ANIONIC OLIGOSACCHARIDE

BACKGROUND OF THE INVENTION

1. Field of the Invention

The invention relates to an iontophoresis device for transcutaneous administration of a medicament active principle of the anionic oligosaccharide type, and in particular of a synthetic anionic oligosaccharide having, inter alia, antithrombotic and/or anticoagulant activities.

2. Description of Related Art

Blood coagulation is a physiological phenomenon which is renowned for its complexity. Certain stimuli, such as contact activation and tissue factors, trigger the successive activation of a series of coagulation factors present in blood plasma.

Irrespective of the nature of the stimulus, the final steps are identical: activated factor X (Xa) activates factor II (also referred to as prothrombin) which, in its activated form (factor IIa, also referred to as thrombin) causes the partial proteolysis of soluble fibrinogen with the release of insoluble fibrin, the main constituent of blood clots.

Under normal physiological conditions, the activity of the coagulation factors is controlled by proteins such as antithrombin III (AT III) and heparin cofactor II (HC II), which are also present in plasma. AT III exerts an inhibiting activation on a number of coagulation factors, and in particular on factors Xa and IIa.

The inhibition of factor Xa or factor IIa therefore constitutes a preferential way of obtaining anticoagulant and antithrombotic activity, since these two factors are involved in the last two steps of coagulation, which are independent of the trigger stimulus.

The pentasaccharide of formula (I)

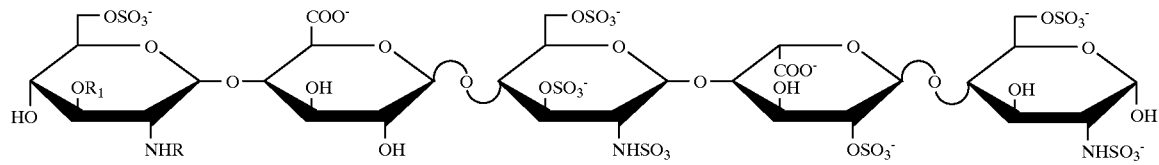

with R representing —COCH$_3$ or —SO$_3$ has a suitable structure for binding to AT III. This compound (R=—SO$_3^-$) was obtained about ten years ago by total chemical synthesis (P. Sinay et al., Carbohydrate Research (1984), 132 C5).

Since then, a number of synthetic anionic oligosaccharides, obtained by total chemical synthesis and having antithrombotic and anticoagulant activities, have been described in the literature (cf., for example, EP-A-0,084,999, EP-A-0,113,599, EP-A-0,165,134, EP-A0,301,618, EP-A-0,454,220 and EP-A-0,529,715).

The anticoagulant and antithrombotic activities which oligosaccharides of this type can have make them useful as active principles in human therapy.

Unfortunately, because of their fairly high molecular weight, their strong anionic charge and their hydrophilic nature, they cannot be administered orally because they cannot cross the gastrointestinal barrier, and they are essentially administered parenterally, for example subcutaneously or intravenously.

It is known that, in such a case, a possible alternative to parenteral administration is transdermic administration, since the compounds do not need to pass through the gastrointestinal tract. However, it has been observed that oligosaccharides of the aforementioned type do not penetrate the skin at a fast enough rate for the systemic concentrations to reach effective therapeutic values.

It is known that iontophoresis can allow certain active principles to be administered transcutaneously to a subject, these active principles generally consisting of compounds having low molecular weight and ionic nature.

To do this, operation is carried out with an aqueous solution or an aqueous gel holding the active principle in an at least partially ionized form, and an electrical signal is applied between, on the one hand, a first electrode, referred to as the active electrode, having the same polarity as the ions of the active principle to be administered and located in contact with a reservoir element which holds the active principle and is placed in contact with a first area of the subject's skin, and on the other hand a second electrode, referred to as the back electrode or passive electrode, having the opposite polarity to the one associated with the active principle, which is placed in contact, directly or via an indifferent electrolyte, with a second area of the subject's skin which is different from the first area. When a current, generated by application of the electrical signal between the electrodes, passes through the circuit produced in this way, the ions of the active principle migrate away from the electrode having the same polarity (active electrode), through the subject's skin and tissue, to the electrode of opposite polarity (back electrode) and are in this way passed into the subject's circulatory system.

SUMMARY OF THE INVENTION

By studying the possibility of transcutaneous passage of derivatives of the oligosaccharide type with anionic nature using the iontophoresis technique, employing reusable electrodes which are commonly used in iontophoresis, for example carbon, platinum or titanium electrodes, the Applicant companies have observed that the transcutaneous fluxes obtained for the said derivatives were very much less than the fluxes which ought to be achieved in order to correspond to therapeutic administration.

The reference EP-A-0,556,112 relates to an iontophoresis device for transcutaneous administration of a medicament active principle, in particular of the anionic type, which includes a negative electrode assembly consisting of a negative electrode, referred to as the active electrode, in contact with a reservoir element containing an electrolyte holding the active principle in an at least partially ionized form, the said reservoir element being arranged in order to ensure, when it is placed in contact with an area of the subject's skin, ionic conducting continuity between the said negative electrode and the said area, a positive electrode assembly consisting either (i) of a positive electrode alone, or preferably (ii) a positive electrode in contact with a receptacle element containing at least one electrolyte, the said receptacle element being arranged in order to ensure, when it is placed in contact with a portion of the subject's skin, ionic conducting continuity between the positive electrode and the said portion, and an electrical signal generator which can be connected to the two electrodes, the negative electrode in contact with the reservoir element being formed at least in part by an ionizable metal compound, the metal ions of which are capable of being electrochemically reduced to the corresponding metal and of forming an electrochemically reversible system with the said metal, so as to constitute a reversible negative electrode, at least when the device is operating, and the generator being arranged in order to apply electrical signals between the electrodes, with an average voltage such that the average current density generated between the electrodes is between 0.03 and 0.5 mA/cm$^2$.

The implementation of the iontophoresis device of reference EP-A-0,556,112 with active principles of the anionic type is illustrated essentially by the use of a product with moderate molecular weight, namely sodium valproate, in a concentration ranging from 5% to 15% by weight, i.e. 0.3 molar to 0.9 molar, which represents more than 50 mg per cm$^2$ of electrode and per mAh of current flowing per cm$^2$ of electrode.

It is known that, when the molecular weight of the active principle increases, the diffusion and the transport number of the ions of the active principle decrease in comparison with the diffusion and the transport number of competing ions, in particular Cl$^-$ ions, which are created at the negative electrode (cathode) based on AgCl. If it is desired to obtain significant passage of the active principle per unit surface area of electrode with current densities that the skin can tolerate, it is necessary to increase the concentrations of active principle and therefore the total quantity of active principle in the reservoir of the electrode, with the drawback of leaving in the said reservoir an unconsumed quantity of the active principle which may amount to more than 99% of the initial quantity. Furthermore, the phenomenon of electro-osmosis, which occurs during any iontophoresis process, generates a flow of water through the skin, circulating from the positive electrode to the negative electrode and counteracting the movement of the ions of anionic active principle to an extent which increases as the size of the said ions increases, that is to say as the molecular weight of the active principle increases.

It was not therefore obviously possible to carry out transcutaneous administration of an anionic active principle having a substantially higher molecular weight than products of the valproate type using an iontophoresis device as described in reference EP-A-0,556,112, while reconciling the requirements of acceptable iontophoretic transcutaneous fluxes of the anionic active principle and the use of a significant fraction of the active principle initially present in the reservoir associated with the negative electrode.

The Applicant companies have demonstrated that it was possible to utilize an iontophoresis device with a reversible negative electrode, of a type comparable with the one described in the reference EP-A-0,556,112, to carry out transcutaneous administration of derivatives of the anionic oligosaccharide type, while obtaining iontophoretic transcutaneous fluxes reaching plasma concentrations having values compatible with therapeutic treatment, and simultaneously using a significant amount of the active principle, if electrical signals were applied between the electrodes with an average voltage such that the average current density generated between the said electrodes has a value ranging from 0.05 to 0.25 mA/cm$^2$, and if the oligosaccharide active principle was initially present in the reservoir element associated with the negative electrode in a quantity substantially smaller than that taught by reference EP-A-0,556,112 for anionic active principles of the valproate type.

The iontophoresis device according to the invention includes a negative electrode assembly consisting of a negative electrode, referred to as the active electrode, in contact with a reservoir element containing an electrolyte holding the active principle in an at least partially ionized form, the said reservoir element being arranged in order to ensure, when it is placed in contact with an area of the subject's skin, ionic conducting continuity between the said negative electrode and the said area, a positive electrode assembly consisting either (i) of a positive electrode alone, or preferably (ii) of a positive electrode in contact with a receptacle element containing at least one electrolyte, the said receptacle element being arranged in order to ensure, when it is placed in contact with a portion of the subject's skin, ionic conducting continuity between the positive electrode and the said portion, and an electrical signal generator which can be connected to the two electrodes, the negative electrode in contact with the reservoir element being formed at least in part by an ionizable metal compound, the metal ions of which are capable of being electrochemically reduced to the corresponding metal and of forming an electrochemically reversible system with the said metal, so as to constitute a reversible negative electrode, at least when the device is operating, and the generator being arranged in order to apply electrical signals between the electrodes, with an average voltage such that the average current density generated between the said electrodes is between 0.03 and 0.5 mA/cm$^2$, which device is characterized in that the active principle present in the reservoir element associated with the negative electrode is chosen from the anionic oligosaccharides represented by the alkali metal or alkaline-earth metal salts of oligosaccharides which consist of from two to twelve saccharide units, of which some or all of the units have their OH groups replaced, at least in part, by functional groups chosen from —OSO$_3^-$, —COO$^-$, —NHSO$_3^-$, —NH-acyl, —OPO$_3^{--}$ and —OT, T representing a hydrocarbon radical, and which have an ionic nature suitable for iontophoretic administration, and in that the said current density has values ranging from 0.05 mA/cm$^2$ to 0.25 mA/cm$^2$, and in that the quantity of active principle initially present in the reservoir element associated with the negative electrode represents from 0.5 to 12 mg per cm$^2$ of electrode and per mAh of current flowing per cm$^2$ of electrode.

Among the metal compounds which may at least in part constitute the negative electrode, non-limiting mention may be made of the compounds AgCl and CuCl.

In particular, the negative electrode may be formed by combining the metal compound with the metal corresponding to it.

The material of the negative electrode may be deposited on a support, which support may consist of an insulator and, in particular, of an insulating plastic such as polypropylene, polyethylene, PVC, polyester or of a metallic or non-metallic electronically conductive material which is resistant to corrosion by the electrolyte holding the active principle in the absence of current, for example silver, titanium, platinum, stainless steel, carbon, graphite and a conductive polymer.

The positive electrode which is used in the process of the invention may be made of a metal or metal alloy such as titanium, platinum, stainless steel, or alternatively of a non-metallic electronically conductive material such as carbon, graphite and a conductive polymer. It is also possible to form the positive electrode, at least in part, by a metal which can be consumed by electrochemical oxidation and, for example, by a metal such as Al, Cu, Mg, Zn and Ag. In this case, the said metal which is consumable by electrochemical oxidation may, in particular, be chosen from those, such as silver, which can form an electrochemically reversible system with the metal ions resulting from the electrochemical oxidation, so as to constitute a positive electrode which is reversible during operation of the device. The material of the positive electrode which is consumable by electrochemical oxidation may be deposited on a support consisting of an insulator and, in particular, of an insulating plastic such as polypropylene, polyethylene, PVC, polyester or alternatively of a metallic or nonmetallic electronically conductive material such as, for example, titanium, platinum, stainless steel, carbon, graphite and a conductive polymer.

The negative electrode and/or the positive electrode may be arranged in order to constitute composite electrodes formed by a composition based on a polymer binder, a pulverulent or fibrous conductive filler, in particular carbon black or short graphite fibres, and the active material of the electrode in divided form, namely, in the case of the negative electrode, the electrochemically reducible metal compound alone or combined with the corresponding metal and, in the case of the positive electrode, the metal or metal alloy chosen to constitute the said electrode. The polymer binder is preferably a polymer based on 1,2-epoxypropane and/or 1,2-epoxybutane, as described in the French patent application No. 94 09231 filed on Jul. 26, 1994 by ELF AQUITAINE and SANOFI.

According to another embodiment of the iontophoresis device according to the invention, which makes it possible to carry out the transcutaneous administration of a given total quantity of the active principle of the anionic oligosaccharide type to a subject, one or other of the negative and positive electrodes is arranged in order to constitute an electrode, referred to as limiting electrode, formed by a limited quantity of an electrochemically consumable material associated either with an electronically conductive support or with an insulating support, the said electrochemically consumable material being either the electrochemically reducible metal compound, when the limiting electrode is the negative electrode, or a metal which is consumable by electrochemical oxidation, in particular a metal such as Al, Mg, Zn and Ag, when the limiting electrode is the positive electrode, and the said electronically conductive support being made of a material which withstands corrosion by the electrolyte associated with the limiting electrode in the absence of current and which, when the limiting electrode is the negative electrode, has a hydrogen overpotential in the presence of the said electrolyte at least equal to that of aluminium, or which is not consumable by electrochemical oxidation, when the limiting electrode is the positive electrode, while the said limited quantity of electrochemically consumable material is chosen so that the quantity of electricity needed for its electrochemical consumption corresponds to the quantity of electricity needed for administering the given total quantity of active principle to the subject, so that the flow of current between the electrodes is practically broken when the consumable material of the limiting electrode has been consumed, and the active principle of the anionic oligosaccharide type is initially present in the reservoir element in contact with the negative electrode in a quantity greater than the given total quantity to be administered to the subject.

One particularly suitable insulating support for the limiting electrode is a support made of an insulating plastic such as polypropylene, PVC, polyethylene or polyester.

As the electronically conductive support for the limiting negative electrode, a support may advantageously be chosen which is made of a material chosen from aluminium, silver, titanium, tantalum, vanadium, stainless steel, zinc, carbon, graphite and a conductive polymer. By way of example, a suitable support for the limiting positive electrode is a support made of a material chosen from platinum, titanium, stainless steel, gold, carbon, graphite and a conductive polymer.

The metallic conductive supports of the negative or positive electrodes may be bulk supports or consist of very thin metal deposits on insulating plastic films. These metal deposits may, for example, be produced by any known technique such as, for example, vacuum metallization or cathodic sputtering.

As non-limiting examples of electrodes which can be used as non-limiting or limiting negative electrodes in the device according to the invention, mention may be made of electrodes based on AgCl or CuCl on a silver, copper, stainless steel, carbon, polypropylene, polyethylene or conductive polymer support. As examples of non-limiting or limiting consumable positive electrodes which can be used in the device according to the invention, non-limiting mention may be made of non-limiting electrodes based on a metal which is consumable by electrochemical oxidation, chosen from Al, Ag, Cu, Mg and Zn, and limiting electrodes based on a metal of this type deposited on an insulating support such as polypropylene or polyester or on a support chosen from titanium, stainless steel, platinum, carbon, graphite and a conductive polymer.

As indicated above, the electrochemically consumable material of the limiting electrode is present in the said electrode in a quantity such that the quantity of electricity needed for its electrochemical consumption corresponds to the quantity of electricity to be used to administer the given total quantity of the active principle of anionic oligosaccharide type to the subject. This latter quantity of electricity, which depends on the iontophoretic system which is used, that is to say on the reaction media in contact with the reversible negative electrode and the positive electrode, the electrical signal applied to the electrodes and the nature of the said electrodes, is determined by means of prior tests for each type of iontophoretic system employed.

The electrical generator applies, between the negative electrode (active electrode) and the positive electrode (back electrode), an electrical signal which may be either an intensiometric signal, that is to say a signal of set average intensity, which is for example constant (intensiostatic signal), or, preferably, a potentiometric signal, that is to say a signal of set average voltage, which is for example constant (potentiostatic signal). The electrical signal of the intensiometric type or the potentiometric type may be continuous or pulsed and permanent or intermittent, with or without temporary polarity reversal. Its frequency can range from 0 to 500 kHz and more particularly from 0 to 100 kHz. When the electrical signal is of a pulsed type, it may have a duty ratio, that is to say a ratio between the duration of the elementary pulse whose repetition forms the pulsed signal, and the time interval separating two consecutive occurrences of this pulse, ranging from 0.05 to 0.95 and more particularly from 0.1 to 0.8.

Advantageously, the average voltage of the signal applied by the generator between the negative electrode and the positive electrode is chosen between 0.1 and 50 volts and more especially between 0.3 and 20 volts, so that the average current density generated between the said electrodes has a value of between 0.05 and 0.25 mA/cm² and preferably between 0.05 and 0.2 mA/cm².

The electrical signal generator of the device according to the invention may be of any known type which makes it possible to generate electrical signals of set average intensity or set average voltage, which are continuous or pulsed and permanent or intermittent, with or without temporary polarity reversal, and which have the characteristics defined above.

The electrolyte which is present in the reservoir element in contact with the negative electrode advantageously contains an aqueous solution or an aqueous gel, which may or may not be adhesive, and which holds the active principle of the anionic oligosaccharide type to be administered in the form of an at least partially ionized salt of an alkali metal such as, for example, sodium or potassium, or a salt of an alkaline-earth metal such as, for example, calcium. Similarly, the electrolyte, which is optionally in contact with the positive electrode, is at least in part in the form of an aqueous solution or an aqueous gel, which may or may not be adhesive. These aqueous solutions or gels may constitute all of the electrolyte present in the reservoir element in question, or may form only a part of the said electrolytes, in which case they are dispersed in a non-aqueous medium which forms the rest of the electrolyte and is chosen so that it does not break the ionic conductive continuity between the electrode and the skin and in order to increase the quality of the adhesion between the electrode and the skin. These aqueous solutions or aqueous gels may be obtained as is well known in iontophoresis techniques. Examples of aqueous gels or of thick aqueous solutions are, in particular, described respectively in references U.S. Pat. No. 4,766,164 and U.S. Pat. No. 3,163,166.

The aqueous medium holding the active principle of the anionic oligosaccharide type, as well as the aqueous medium constituting the electrolyte associated with the positive electrode, when the said electrolyte is used, may if necessary hold agents capable of promoting the transcutaneous passage of the active principle, for example vasodilators and/or amphiphilic agents, of which non-limiting examples that may be mentioned are compounds of the alcohol type or of the ester type. These agents are used in concentrations which allow good solubility of the active principle in the medium.

As indicated above, the quantity of active principle of the anionic oligosaccharide type initially present in the reservoir element associated with the negative electrode represents from 0.5 mg to 12 mg, and preferably from 1 mg to 8 mg per cm² of the said electrode and per mAh of current flowing per cm² of this electrode.

It is possible to introduce the active principle to be administered not only into the reservoir element associated with the negative electrode, but also into the receptacle element associated with the positive electrode, and in this case the negative electrode and the positive electrode of the iontophoresis device consist of a reversible electrode based on the reducible ionizable metal compound and the metal corresponding to it, for example a reversible electrode based on the pair Ag/AgCl. By reversing the polarity of the electrical signals applied to the electrodes, this makes it possible to administer the active principle alternately from the reservoir element and from the receptacle element.

In this case, the quantity of active principle of the anionic oligosaccharide type initially present in the reservoir element associated with each of the electrodes represents from 0.5 mg to 6 mg and preferably 0.5 mg to 4 mg per cm² of electrode and per mAh of current flowing per cm² of electrode.

The anionic oligosaccharides which the invention concerns consist of alkali metal or alkaline-earth metal salts, in particular sodium, potassium or calcium salts, of compounds which consist of from two to twelve units, and more particularly from three to eight saccharide units, of which some or all units have their OH groups at least in part replaced by functional groups such as, for example, $—OSO_3^{31}$, $—COO^-$, $—NHSO_3^-$, $—NH$-acyl, $—OPO_3^{--}$, $—OT$ where T represents a hydrocarbon radical and, in particular, an aliphatic or aromatic hydrocarbon radical, $—OT$ being in particular an alkoxy functional group, and which have an ionic nature suitable for iontophoretic administration. The said oligosaccharides are more particularly anionic oligosaccharides obtained by total chemical synthesis.

In particular, the said oligosaccharides may be chosen from:

the synthetic oligosaccharides described in reference EP-A-0,084,999, which consist of from 2 to 12 alternate uronic-acid (glucuronic or iduronic) and glucosamine monosaccharide units and, further to OH groups, contain $—OSO_3^{31}$, $—NHSO_3^-$ and $—N$-acyl, in particular $—N$-acetyl, functional groups and, in certain cases, alkoxy, in particular methoxy, groups as replacement for the anomeric OH groups. Examples of oligosaccharides of this type are pentasaccharides having antithrombotic and/or anticoagulant properties, which include the compounds represented by formula (I) given above;

the synthetic oligosaccharides having antithrombotic activity which are described in reference EP-A-0,165,134, which consist of uronic-acid and glucosamine monosaccharide units and contain $—OSO_3^-$ and $—O—PO_3^{--}$ functional groups;

the pentasaccharides having antithrombotic and/or anticoagulant properties which described in reference EP-A-0,301,618, which consist of uronic-acid units and glucosamine units and have an $—OSO_3^-$ group at position 3 of the glucosamine structural unit;

the synthetic oligosaccharides having antithrombotic and/or anticoagulant properties are described in reference EP-A-0,454,220, which are derivatives of uronic acids and of glucose having a specific trisaccharide chain sequence and including O-alkyl or $—O—SO_3^-$ functional groups;

the synthetic sulphated glycosaminoglycan derivatives having antithrombotic properties and having an inhibiting activity on the proliferation of smooth muscular cells, which are described in reference EP-A-0,529,715, for which the $—NHSO_3^-$, N-acetate or OH functional groups have been replaced by alkoxy, aryloxy, aralkyloxy or $—O—SO_3^-$ groups;

the synthetic 3-deoxy heparin derivatives having antithrombotic activity which are described in French patent application No. 93 04769 filed on Apr. 22, 1993 by ELF SANOFI and AKZO, which consist of uronic-acid units and glucosamine units and for which the $—NHSO_3^-$, N-acetate functional groups of the glucosamine unit, and optionally the OH groups of the uronic-acid and glucosamine units have been replaced by alkoxy or $—O—SO_3^-$ groups;

the synthetic oligosaccharides described in reference EP-A-0,113,599, which consist of uronic-acid (glucuronic or iduronic) and D-galactosamine monosaccharide units.

The anionic oligosaccharide used according to the invention are, in particular, tri-, tetra-, penta- or hexasaccharides and, more especially, pentasaccharides, in particular pentasaccharides of the following formula (II):

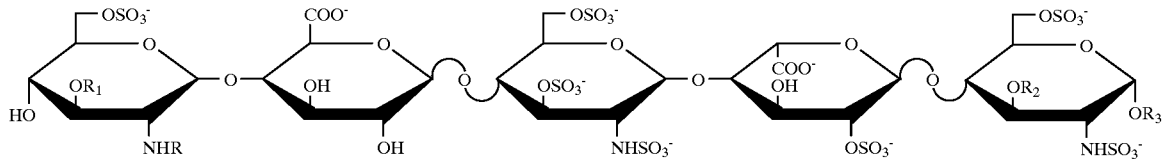

in which R is an —$SO_3^-$ or acyl, in particular acetyl, group, $R_1$ and $R_2$, which are identical or different, denote H or —$SO_3$ and $R_3$ represents H or a lower alkyl radical, in particular —$CH_3$.

The device according to the invention can be produced from any known iontophoresis device which has been modified so that (i) its negative electrode is a reversible negative electrode, the positive electrode being either a conventional positive electrode or an irreversible or reversible consumable positive electrode, and the reservoir element associated with the negative electrode holding the active principle of the anionic oligosaccharide type in an at least partially ionized form, (ii) its electrical signal generator is arranged in order to apply, between the electrodes, electrical signals having an average voltage such that the average current density generated between the electrodes is between 0.05 and 0.25 $mA/cm^2$ and preferably between 0.05 and 0.2 $mA/cm^2$ and (iii) the quantity of active principle of the anionic oligosaccharide type initially present in the reservoir element associated with the negative electrode or in the reservoir or receptacle element associated with the negative or positive electrode has a value as indicated above.

If appropriate, the negative electrode or the positive electrode may be arranged as indicated above in order to constitute a limiting electrode.

In particular, the device according to the invention may be a portable self-contained device, to be fixed by a bracelet or possibly to be stuck on to the skin, comprising electrodes each having an area of less than 50 $cm^2$ and more particularly between 1 and 30 $cm^2$ and a miniaturized electrical signal generator. Thus, a self-contained portable device according to the invention can have a structure similar to those of the self-contained portable iontophoresis devices described, for example, in references U.S. Pat. No. 4,325,367, EP-A-0,060,452 and FR-A-2,509,182 with the reservation that the negative electrode of the said device is a reversible negative electrode and the electrical signal generator and the reservoir element associated with each electrode are arranged as indicated above.

The negative electrode may, for example, be an electrode based on AgCl or CuCl on a silver, copper, carbon, polypropylene, polyethylene or conductive-polymer support. The positive electrode may be a conventional positive electrode, for example an electrode made of a metal or metal alloy such as titanium, platinum, stainless steel or alternatively of a non-metallic electronically conductive material such as carbon or graphite, or alternatively an irreversible or reversible consumable positive electrode, for example an electrode made of a metal such as Al, Cu, Mg, Zn and Ag, optionally deposited on an insulating support such as polypropylene or polyester or on a support chosen from titanium, stainless steel, platinum, carbon, graphite and a conductive polymer. The said negative and positive electrodes, one and/or other of which may be arranged as indicated above in order to constitute a limiting electrode, each have an area of less than 50 $cm^2$ and more particularly between 1 and 30 $cm^2$.

When the negative electrode assembly and the positive electrode assembly are fixed to the skin by means of an adhesive, this can be done by providing that face of the reservoir element of each electrode assembly which is intended to come into contact with the skin, or an area surrounding the said face, with a layer of an ion-conducting adhesive.

When it is equipped with at least one negative electrode based on the pair Ag/AgCl and preferably has a negative electrode and a positive electrode based on the said pair Ag/AgCl, the iontophoresis device according to the invention may further include an assembly for monitoring the degree of progress of the transcutaneous administration of the active principle, as described in French Patent Application No. 94 10541 filed on Sep. 2, 1994 by ELF AQUITAINE and SANOFI.

The invention is illustrated by the following examples which are given without implying any limitation.

EXAMPLE 1

Study of the transdermic passage of a sodium pentasaccharide salt by iontophoresis at constant voltage.

The pentasaccharide used corresponded to the one having the previously given formula (I), where R denotes —$SO_3^-$.

The operation was carried out in iontophoresis cells of identical structure. Each iontophoresis cell consisted of three coaxial adjacent cylindrical compartments having a cross-sectional area of 2 $cm^2$, namely, in this order, a donor compartment, a receiver compartment and a back-electrode compartment, these three compartments being each separated from the following one in leak-tight fashion by a piece of nude rat skin (OFA/hr/hr) used as a membrane for studying the transcutaneous diffusion. The donor compartment, having a volume of 0.5 ml, held a 2% by weight aqueous solution of the sodium salt of the aforementioned pentasaccharide having an antifactor Xa activity of 0.65 "Golden Standard" units per microgram, the quantity of pentasaccharide representing 10 mg per 2 $cm^2$ of active surface area of the electrode. The receiver compartment, having a volume of 10 ml, held physiological saline solution supplemented with 500 ppm of $NaN_3$ and was stirred using a magnetic bar. The back-electrode compartment, which was identical to the donor compartment, held 0.5 ml of a 2% by weight aqueous solution of sodium chloride as well as 500 ppm by weight of $NaN_3$. At its opposite end from the receiver compartment, the donor compartment was equipped with a negative electrode. In the same way as the donor compartment, the back-electrode compartment was equipped with a positive electrode (back electrode).

The rat skin samples had had the subcutaneous tissue removed and had been preserved by freezing at −40° C. until they were mounted in the iontophoresis cell, with the dermic faces turned towards the receiver compartment, after they had been placed for 15 minutes in physiological saline solution supplemented with 500 ppm of $NaN_3$.

For each of the tests which were carried out, four identical iontophoresis cells were started simultaneously. The active exchange surface area was 2 $cm^2$ for each skin.

A pulsed current generator made it possible to set up an electrical signal of the potentiostatic type between the electrodes of the four cells, mounted in parallel, with a peak voltage equal to 2.2 volts and a duty ratio of 50% (i.e. an average voltage of 1.1 volts) and a frequency of 25 kHz.

The pulsed current produced by the generator was applied for 6 hours, the electrode of the donor compartment of each cell being connected to the negative pole of the said generator, and the back electrodes to the positive pole.

At the end of the said time, an aliquot of the medium contained in the receiver compartment was withdrawn and the quantity of pentasaccharide that had passed through the skin separating the donor and the receiver compartments of each cell was determined by assay. A second sample was taken 24 hours after the start of each experiment, i.e. 18 hours after the electrical signal had stopped.

Five tests 1a to 1e were carried out as follows:

Test 1a: The negative electrode and the positive electrode consisted of a titanium film having a thickness equal to 10 μm. No voltage was applied to the electrodes, in order to determine the passive transcutaneous diffusion.

Test 1b: The negative electrode and the positive electrode consisted of a graphite sheet having a thickness of 60 μm.

Test 1c: The negative electrode and the positive electrode consisted of a titanium film having a thickness equal to 10 μm.

Test 1d to 1e: The negative electrode consisted of a silver film having a thickness of 15 μm, chlorided beforehand on one face in order to contain a silver chloride layer corresponding to 1.8 $mAh/cm^2$, whereas the positive electrode consisted of a silver film having a thickness of 15 μm, very slightly chlorided on one face (a quantity of silver chloride corresponding to 0.1 $mAh/cm^2$, the chlorided face of each electrode being on the side adjacent to the rat skin membrane.

The silver films were chlorided electrochemically by passing a direct current of 5 $mA/cm^2$, while each silver film, one of the faces of which was protected with an insulating adhesive plastic film, was immersed in a 0.1 N hydrochloric acid bath and constituted the positive pole with respect to a graphite electrode immersed in the same HCl bath, the quantity of current was monitored by a coulometer mounted in series in the circuit, in order to form the desired quantity of silver chloride on the silver film.

In tests Ia to Id, the donor and the receiver compartments of each cell held a 0.06 molar buffer composition based on sodium monohydrogenphosphate and dihydrogenphosphate in equimolar quantities, so as to keep the pH in the said compartments at a value of about 7. In test 1e, no buffer was used. In tests 1d and 1e, the average current density generated between the electrodes was equal to about 0.20 $mA/cm^2$.

For each of the tests, the average antifactor Xa activity per ml of medium was determined for the aliquots taken from the receiver compartments of the four cells, this activity being representative of the quantity of pentasaccharide that had diffused into these compartments after 6 hours of applying the current and 24 hours after the start of each experiment, i.e. 18 hours after stopping the said current.

The assay of the pentasaccharide in the receiver compartment was based on investigating its antifactor Xa activity. The assay was carried out either directly on the medium sampled from the receiver compartment or after dilution, using a ROTACHROM HEPARIN 8® assay kit, a complementary buffer for the assay instrument and bovine antithrombin III, these various elements being supplied by the company STAGO, using a HITACHI 717 assay instrument. The calibration curve was established using a "Golden Standard" pentasaccharide solution to which an antifactor Xa activity equal to 13 units per ml was assigned.

The results obtained are collated in Table I.

TABLE I

| TEST | 1a | 1b | 1c | 1d | 1e |
|---|---|---|---|---|---|
| Average voltage (volts) | 0 | 1.1 | 1.1 | 1.1 | 1.1 |
| Nature of the negative electrode | Titanium | Graphite | Titanium | Ag/AgCl | Ag/AgCl |
| Antifactor activity Xa/ml at 6 hours | <0.1 | 0.70 | 0.50 | 9.1 | 18.1 |
| % variation from mean | | 38 | 54 | 41 | 46 |
| Fraction of active principle used (%) | ~zero | 0.1 | 0.08 | 1.4 | 2.8 |
| Antifactor activity Xa/ml at 24 hours | 0.25 | 1.13 | 0.95 | 9.7 | 21.4 |
| % variation from mean | 60 | 45 | 51 | 43 | 39 |
| Fraction of active principle used (%) | ~zero | 0.2 | 0.15 | 1.5 | 3.3 |

Since the level of antifactor Xa activity reflected the concentration of pentasaccharide in the receiver compartment, inspection of Table I clearly shows that the quantities of pentasaccharide that had diffused into the receiver compartment by iontophoresis are very small and similar to the passive transport when irreversible electrodes such as graphite or titanium are used, whereas the said quantities increase very greatly when Ag/AgCl negative electrodes (reversible electrodes) are used, even in the presence of a buffer. Unlike non-consumable electrodes such as titanium or graphite, these reversible electrodes make it possible to avoid hydrolysis of water and therefore significant changes in pH in the course of treatment, at both the negative and the positive electrodes. The presence of substances having a buffer effect in the donor compartments is therefore no longer necessary, which constitutes an additional advantage of reversible electrodes. As can be seen on reading test 1e, the transdermic fluxes under iontophoresis which were obtained in the absence of a buffer are increased further compared to all the other tests (137 $\mu g/cm^2$ per mAh).

EXAMPLE 2

Study of the transdermic passage of a sodium pentasaccharide salt by iontophoresis at set intensity The procedure as described in Example 1 was carried out, but with the following modifications:

implementation of the iontophoresis by setting a constant intensity through each cell use of a continuous current instead of a pulsed current the absence of buffer in the donor and back-electrode compartments in test 2d, because these compartments are equipped with electrodes of the Ag/AgCl type, which avoid hydrolysis of water.

The procedure was carried out while setting a constant direct current of 0.4 mA, i.e. 0.2 $mA/cm^2$, for the electrodes of each of the 4 iontophoresis cells, over a period of 6 hours, using a generator making it possible to set a constant intensity irrespective of the voltages generated across the terminals of each cell.

The direct current of constant intensity equal to 0.4 mA produced by the generator was applied for 6 hours, the donor compartment of each cell being connected to the negative pole of the said generator, and the back electrodes to the positive pole.

For each of the tests 2a to 2d, the average antifactor Xa activity per ml of receiver medium was determined for the aliquots taken from the receiver compartments, this activity being representative of the quantity of pentasaccharide having diffused therein after 6 hours of applying the current and 24 hours after the start of each experiment, i.e. 18 hours after stopping the said current.

The results obtained are collated in Table II

TABLE II

| TEST | 2a | 2b | 2c | 2d |
|---|---|---|---|---|
| Average current density (mA/cm$^2$) | 0 | 0.2 | 0.2 | 0.2 |
| Nature of the negative electrode | Titanium | Graphite | Titanium | Ag/AgCl |
| Antifactor activity Xa/ml at 6 hours | 0.12 | 6 | 3.2 | 18.1 |
| % variation from mean | | 35 | 42 | 22 |
| Fraction of active principle used (%) | ~zero | 0.09 | 0.49 | 2.8 |
| Antifactor activity Xa/ml at 24 hours | 0.6 | 5.8 | 4.9 | 24 |
| % variation from mean | 60 | 45 | 51 | 18 |
| Fraction of active principle used (%) | 0.09 | 0.9 | 0.75 | 3.7 |

The total diffused quantities, expressed in $\mu$g per cm$^2$ for each of the tests, are respectively equal to 4.64 (test 2a), 45 (test 2b), 38 (test 2c) and 185 (test 2d), i.e. 154 $\mu$g/cm$^2$ per mAh for the Ag/AgCl electrodes.

Even though, in comparison with the previous tests carried out at constant voltage, the diffusion under iontophoresis has become more significant compared to the passive diffusion for the graphite and titanium electrodes, the performance of the chlorided silver electrodes remain very much superior.

EXAMPLE 3

Administration in minipigs of pentasaccharide sodium salt by iontophoresis at a set current density Specialists consider minipigs of the YUCATAN strain to be an excellent animal model for studying the administration in man of medicaments by iontophoresis. This is because the skin structure of this animal is very similar to that of human skin.

The following tests were carried out on the aforementioned minipig with the aim of comparing the administration of the sodium salt of the pentasaccharide used in the previous examples by iontophoresis with administration by subcutaneous or intravenous injection.

For these tests, pairs of adhesive electrode sets were formed, each pair having a donor electrode assembly formed by a reversible negative electrode (active electrode) in contact with a first reservoir element holding the pentasaccharide to be administered, and a passive electrode assembly formed by a positive electrode (back electrode) in contact with a second reservoir element (receptacle element) holding an indifferent electrolyte.

BRIEF DESCRIPTION OF THE FIGURE DRAWING

Each electrode assembly had a structure similar to the one that is schematically represented, by way of non-limiting example, in the figure.

DETAILED DESCRIPTION OF THE PREFERRED EMBODIMENT

Figure 1:
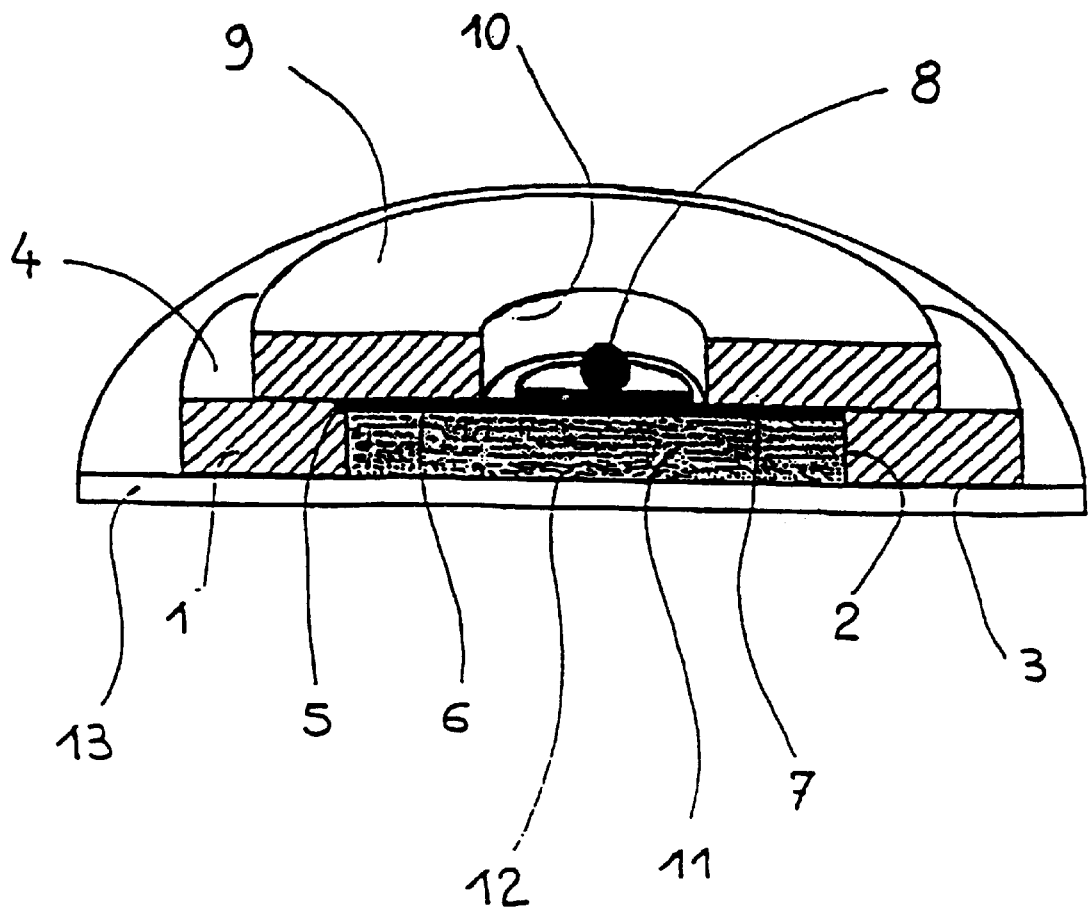

Referring to the figure, each electrode assembly included a disc 1 of polyethylene foam having an axial cylindrical recess 2, the said disc having an adhesive face 3 and a non-adhesive face 4, each of the said faces having the shape of an annular area with a width of two centimetres. The end 5 of the recess in the disc, on the non-adhesive face side, was closed off by an electrode 6 in the form of a silver disc chlorided on one of its faces, the said disc having a cross-sectional area of 20 cm$^2$. The chlorided face 7 of the electrode disc is turned towards the interior of the recess. The non-chlorided face of the said disc had a contact connector 8 of the push-button type welded to the said face by means of an electronically conductive adhesive, and was pressed against a polyethylene foam support disc 9, coaxial with the disc 1 and having an axial recess 10 to allow access to the contact connector 8. The said support disc, having a diameter intermediate between that of the electrode 6 and the disc 1, was bonded onto the non-adhesive face of the latter disc. The recess 2 in the disc 1 was filled with a conductive hydrogel 11 forming the reservoir element. The adhesive face 3 of the disc 1 was coated with a pressure-sensitive adhesive designed to be applied to the skin, the said face 3 and the face 12 adjacent to the reservoir element 11 being initially covered with a peelable non-stick polyester protective film which was removed before application to the skin.

In the donor electrode assembly, the negative electrode (active electrode) of chlorided silver contained a quantity of silver chloride equivalent to 1.8 mAh/cm$^2$, thus allowing the electrode to sustain the quantity of current flowing through the electrodes over the duration of the iontophoretic treatment, namely 1.2 mAh/cm$^2$. The reservoir element associated with the negative electrode was filled over a thickness of 2 mm, i.e. a quantity of 4 g over the 20 cm$^2$ of electrode, with a hydrogel based on xanthan and carob extract having 3% of dry extract and containing 2% by weight of sodium salt of the pentasaccharide of formula (I) given above. The donor electrode assembly therefore contained 80 mg of pentasaccharide in a ratio of 4 mg/cm$^2$ for each of the animals which were treated.

In the passive electrode assembly, the positive electrode (back electrode) made of chlorided silver contained a quantity of silver chloride equivalent to 0.1 mAh/cm$^2$, and the reservoir element associated with this electrode consisted of the same hydrogel as the one present in the donor electrode assembly, but without pentasaccharide and instead holding 4% by weight of NaCl.

An electrical signal generator, connectable to the electrodes of each electrode assembly pair, made it possible to deliver between the said electrodes a pulsed electrical signal of controlled intensity, having a frequency of 25 kHz and a duty ratio equal to 50%.

Five days before each test, the animals were catheterized in the two jugulars, as is well known for any experimentation in medicament administration, in order to make it possible to take regular blood samples intended for assaying the antifactor Xa activities and thereby to evaluate the quantities of active principle that passed through the skin to enter the circulatory system and therefore to check the effectiveness of the iontophoresis treatment.

The animals, fasted from the day before the experiments, were placed in specialized hammocks. A pair of electrode assemblies, with their peelable protective film removed beforehand, were stuck by simple pressure on the back of each animal, cleaned beforehand using a wet tissue, on either side of the spinal column, and, using cables fitted with clips designed for the contact connectors fitted for this purpose, the negative electrode of the donor electrode assembly was connected to the negative pole of the generator, and the back electrode of the passive electrode assembly was connected to the positive pole of the said generator.

The generator was used to set up a current of 4.8 mA (i.e. a current density of 0.20 mA/cm$^2$) between the positive and negative electrodes of each pair of electrode assemblies stuck to the animal, for a period of 6 hours, and various blood samples were taken with an H STAGO® diatube periodically until 30 hours after the start of each experiment, i.e. 25 hours after the end of the iontophoretic treatment. The iontophoretic test was reproduced on five male minipigs with an average weight of 11.4 kg.

Further to the tests of administering the active principle by iontophoresis, implemented as described above (test 3b), comparative tests 3a, 3c and 3d were also carried out as follows, each test being reproduced from two to four minipigs, as in the case of the iontophoretic administration:

test 3a: fitting the electrode assemblies as in the iontophoresis test 3b, but without applying a current, test 3c: bolus intravenous injection of 0.240 mg/kg of pentasaccharide in injectable solution, test 3d: subcutaneous injection of 0.200 mg/kg of pentasaccharide in injectable solution.

In these tests 3a, 3c and 3d, a number of blood samples were taken periodically, up to 30 hours after the start of each experiment, as in the case of the iontophoretic treatment in test 3b.

The plasma levels of the various blood samples, expressed in "Golden standard" units of antifactor Xa, are indicated in Table III for the purpose of comparison with the average plasma levels obtained for animals of the same strain and with the same weight treated with the same active principle under the test conditions according to the invention (test 3b) and the comparative tests (tests 3a, 3c and 3d).

TABLE III

| Nature of the treatment | TEST | | | |
|---|---|---|---|---|
| | 3a Passive | 3b Iontophoresis | 3c I.V. injection | 3d Subcutaneous injection |
| Number of minipigs treated | 2 | 5 | 4 | 4 |
| Current density (mA/cm$^2$) | 0 | 0.20 | | |
| Plasma level at 0 minutes | 0 | 0 | 0 | 0 |
| Plasma level at 5 minutes | 0 | no assay | 1.04 ± 0.12 | no assay |
| Plasma level at 15 minutes | 0 | 0.06 ± 0.04 | 0.91 ± 0.13 | 0.11 ± 0.04 |
| Plasma level at 30 minutes | 0 | 0.15 ± 0.12 | 0.65 ± 0.11 | no assay |
| Plasma level at 1 hour | 0 | 0.31 ± 0.15 | 0.53 ± 0.10 | 0.17 ± 0.01 |
| Plasma level at 2 hours | 0 | 0.45 ± 0.2 | 0.30 ± 0.09 | 0.22 ± 0.04 |
| Plasma level at 4 hours | 0 | 0.64 ± 0.18 | 0.29 ± 0.08 | 0.26 ± 0.06 |
| Plasma level at 6 hours | 0 | 0.74 ± 0.16 | 0.22 ± 0.09 | 0.24 ± 0.01 |
| Plasma level at 8 hours | 0 | 0.52 ± 0.13 | 0.17 ± 0.06 | 0.15 ± 0.07 |
| Plasma level at 12 hours | 0 | 0.4 ± 0.08 | 0.07 ± 0.05 | 0.08 ± 0.03 |
| Plasma level at 24 hours | 0 | 0.11 ± 0.03 | 0 | 0 |
| Plasma level at 30 hours | 0 | 0 | 0 | 0 |

Comparing the results in Table III shows that the iontophoretic treatment carried out according to the invention leads to higher plasma levels, expressed in terms of antifactor Xa, than can be obtained with intravenous or subcutaneous injections. The plasma levels rise fairly quickly and uniformly during the treatment and decrease slowly after the current is stopped.

Administering this type of active principle iontophoretically, especially if this is spread over a slightly longer daily period and with even lower current densities, makes it possible to obtain a plasma concentration of active principle which leads to good antithrombotic cover, expressed in terms of antifactor Xa, over a relatively long time and without passing through high peak plasma levels.

Comparing the areas under the curves representing the change in the plasma levels over time during the various treatments will allow a pharmacokinetics specialist to calculate, as a function of the animals' weight, the quantities of pentasaccharide which have actually been administered by iontophoresis. In the case of test 3b, this quantity was estimated at 7±1.3 mg for the 20 cm$^2$, i.e. 350 $\mu$g/cm$^2$ for 1.2 mAh/cm$^2$, i.e. 292 $\mu$g/cm$^2$ for 1 mAh/cm$^2$.

The bioavailability, that is to say the level of active principle actually administered, normalized to the quantities of active principle present in the electrodes, is therefore about 9%, which is higher than the utilized fractions observed for in vitro tests.

EXAMPLE 4

Administration to minipigs of the sodium salt of a pentasaccharide by iontophoresis with set current density with periodic reversal of the current direction.

The following iontophoretic administration tests were carried out on 4 minipigs by using the same current generator and the same type of electrodes as in Example 3, and by applying the following conditions:

The electrodes, with the same structure as in Example 3, had an active surface area of 20 cm$^2$. The electrodes themselves consisted of 15 $\mu$m thick silver films chlorided by electrolytic oxidation in a ratio of 0.5 mAh of silver chloride per cm$^2$. The reservoirs, also measuring 20 cm$^2$, consisted of a sheet of blotting paper made of cellulose fibres supplemented with polypropylene fibrils, impregnated to a level of 50 mg/cm$^2$ with an aqueous solution containing 2% by weight of pentasaccharide and 0.2% by weight of NaCl. Each electrode, the anode and the cathode, contained in all 1 g of solution, i.e. 20 mg of pentasaccharide (1 mg/cm$^2$) for an active surface area of 20 cm$^2$. 40 mg of pentasaccharide were therefore engaged in all per animal.

The current generator delivered a constant intensity of 2.5 mA, i.e. 125 $\mu$A/cm$^2$ of direct current with regular reversals of the current direction every 30 minutes for a total time of 8 hours, corresponding to the passage of 1 mA/cm$^2$ of direct current.

Each of the electrodes, having identical structure and composition, was therefore operated alternately as the cathode and then as the anode, the presence of sodium chloride in each of the reservoirs ensuring their permanent operation as a reversible electrode, thus avoiding any parasitic reaction of hydrolysis (with a change in the pH) or oxidation/reduction of the active principle.

In test 4a, involving 3 animals with an average weight of 11.8 kg, the electrodes were put in place but not connected to the current generator, whereas for all the tests 4b, which concerned 4 animals with an average weight of 12.3 kg, the current of 2.5 mA was applied for 8 hours with automated reversal of the current direction every half hour.

In tests 4a and 4b, a number of blood samples were taken periodically up to 30 hours after the start of each experiment, as in Example 3.

The plasma levels of the various samples are indicated in Table IV for the purpose of comparing tests 4a and 4b with one another and with the results of the tests carried out in Example 3, in particular tests 3c and 3d which correspond to intravenous and subcutaneous injections.

Comparing the area under the curve representing the change in the plasma levels over time for test 4b with that of tests 3c and 3d allows a pharmacokinetic specialist to evaluate with high precision the average quantity of pentasaccharide administered during the treatment. This quantity is zero for the passive test 4a and 8.45±1.5 mg of pentasaccharide for test 4b.

TABLE IV

| | TEST | |
| --- | --- | --- |
| Nature of the treatment | 4a Passive | 4b Iontophoresis |
| Number of animals treated | 2 | 4 |
| Current density (mA/cm$^2$) | 0 | 0.125 |
| Initial plasma level | 0 | 0 |
| Plasma level at 30 minutes | 0 | 0.11 ± 0.05 |
| Plasma level at 1 hour | 0 | 0.16 ± 0.05 |
| Plasma level at 2 hours | 0 | 0.28 ± 0.1 |
| Plasma level at 4 hours | 0 | 0.64 ± 0.2 |
| Plasma level at 6 hours | 0 | 0.57 ± 0.18 |
| Plasma level at 8 hours | 0 | 0.59 ± 0.15 |
| Plasma level at 10 hours | 0 | 0.61 ± 0.16 |
| Plasma level at 12 hours | 0 | 0.58 ± 0.05 |
| Plasma level at 16 hours | 0 | 0.2 ± 0.05 |
| Plasma level at 26 hours | 0 | 0.14 ± 0.02 |
| Plasma level at 30 hours | 0 | 0.05 ± 0.02 |

In comparison with the previous test, for which 80 mg of pentasaccharide were engaged, better bioavailability is observed, i.e. about 21% for test 4b as against about 9% for test 3b. A better electrical efficiency is also observed since the quantity of pentasaccharide administered per mAh was 292 μg/cm$^2$ for test 3b whereas it is 372 μg/cm$^2$ for test 4b.

This approach, using periodic and balanced reversal of the current, which makes it possible to consume, in each reservoir, some of the chloride ions generated by the reduction of silver chloride during the preceding phase, reduces the competition of the chloride ions with respect to the therapeutic ions and makes it possible to decrease the quantities of active principle per surface unit. It has further shown the interest to make use of reversible electrodes which prevent the oxidation/reduction reactions that could affect the active principle which is alternately in an anodic and then cathodic compartment.

As the iontophoresis devices can now be miniaturized and built to be easily portable for everyday life, the iontophoresis carried out according to the invention forms a particularly interesting galenic way for the delivery of pentasaccharides of the above-disclosed type and more generally of analogous or closely related anionic oligosaccharides.

We claim:

1. Iontophoresis device for transcutaneous administration of a medicament active principle of the anionic type, comprising a negative electrode assembly consisting of a negative electrode, referred to as the active electrode, in contact with a reservoir element containing an electrolyte holding the active principle in an at least partially ionized form, the said reservoir element being arranged in order to ensure, when it is placed in contact with an area of the subject's skin, ionic conducting continuity between the said negative electrode and the said area, a positive electrode assembly consisting either (i) of a positive electrode alone, or preferably (ii) of a positive electrode in contact with a receptacle element containing at least one electrolyte, the said receptacle element being arranged in order to ensure, when it is placed in contact with a portion of the subject's skin, ionic conducting continuity between the positive electrode and the said portion, and an electrical signal generator which can be connected to the two electrodes, the negative electrode in contact with the reservoir element being formed at least in part by an ionizable metal compound, the metal ions of which are capable of being electrochemically reduced to the corresponding metal and of forming an electrochemically reversible system with the said metal, so as to constitute a reversible negative electrode, at least when the device is operating, and the generator being arranged in order to apply electrical signals between the electrodes, with an average voltage such that the average current density generated between the said electrodes is between 0.03 and 0.5 mA/cm$^2$, which device is characterized in that the active principle present in the reservoir element associated with the negative electrode is chosen from the anionic oligosaccharides represented by the alkali metal or alkaline-earth metal salts of oligosaccharides which consist of from two to twelve saccharide units, of which some or all of the units have their OH groups replaced, at least in part, by functional groups chosen from —OSO$_3^-$, —COO$^-$, —NHSO$_3^-$, —NH-acyl, —OPO$_3^{--}$ and —OT, T representing a hydrocarbon radical, and which have an ionic nature suitable for iontophoretic administration, and in that the said current density has values ranging from 0.05 mA/cm$^2$ to 0.25 mA/cm$^2$, and in that the quantity of active principle initially present in the reservoir element associated with the negative electrode represents from 0.5 to 12 mg per cm$^2$ of electrode and per mAh of current flowing per cm$^2$ of electrode.

2. Device according to claim 1, wherein the said anionic oligosaccharides are obtained by total chemical synthesis.

3. Device according to claim 1 wherein the metal compound which may at least in part constitute the negative electrode is chosen from the compounds AgCl and CuCl.

4. Device according to claim 1, wherein the material of the negative electrode is deposited on a support, which support consists of an insulator and, in particular, of an insulating plastic such as polypropylene, polyethylene, PVC, polyester or of a metallic or non-metallic electronically conductive material which is resistant to corrosion by the electrolyte holding the active principle in the absence of current, for example silver, titanium, platinum, stainless steel, carbon, graphite and a conductive polymer.

5. Device according to claim 4, wherein the negative electrode is based on the pair Ag/AgCl.

6. Device according to claim 1, wherein the positive electrode is made of a metal or metal alloy such as titanium, platinum, stainless steel or alternatively of a non-metallic electronically conductive material such as carbon or graphite, or consists at least in part of a metal which can be consumed by electrochemical oxidation, for example a metal such as Al, Cu, Mg, Zn and Ag, the said metal which is consumable by electrochemical oxidation being, in particular, chosen from those which can form an electrochemically reversible system with the metal ions resulting from the electrochemical oxidation, so as to constitute a reversible positive electrode.

7. Device according to claim 6, wherein the positive electrode is based on the pair Ag/AgCl.

8. Device according to claim 1, for administering a given total quantity of the active principle of the anionic oligosaccharide type to the subject, characterized in that one or other of the negative and positive electrodes is arranged in order to constitute an electrode, referred to as limiting electrode, formed by a limited quantity of an electro-chemically consumable material associated either with an electronically conductive support or with an insulating support, the said electrochemically consumable material being either the electrochemically reducible metal compound, when the limiting electrode is the negative electrode, or a metal which is consumable by electrochemical oxidation, in particular a metal such as Al, Mg, Zn and Ag, when the limiting electrode is the positive electrode, and the said electronically conductive support being made of a material which withstands corrosion by the electrolyte associated with the limiting electrode in the absence of current and which, when the limiting electrode is the negative electrode, has a hydrogen overpotential in the presence of the said electrolyte at least equal to that of aluminium, or which is not consumable by electrochemical oxidation, when the limiting electrode is the positive electrode, while the said limited quantity of electrochemically consumable material is chosen so that the quantity of electricity needed for its electrochemical consumption corresponds to the quantity of electricity needed for administering the given total quantity of active principle to the subject, so that the flow of current between the electrodes is practically broken when the consumable material of the limiting electrode has been consumed, and in that, at the start of the operation, the active principle of the anionic oligosaccharide type is present in the reservoir element in contact with the negative electrode in a quantity greater than the given total quantity to be administered to the subject.

9. Device according to claim 1, wherein the electrical signal generator applies between the negative electrode and the positive electrode an intensiometric signal, that is to say a signal of set average intensity, or a potentiometric signal, that is to say a signal of set average voltage, the said electrical signal being continuous or pulsed and permanent or intermittent, with or without temporary polarity reversal, and having a frequency ranging from 0 to 500 kHz and more particularly from 0 to 100 kHz.

10. Device according to claim 9, wherein the electrical signal is a pulsed signal having a duty ratio, that is to say a ratio between the duration of the elementary pulse whose repetition forms the pulsed signal, and the time interval separating two consecutive occurrences of this pulse, ranging from 0.05 to 0.95 and more particularly from 0.1 to 0.8.

11. Device according to claim 9 wherein the signal applied between the negative electrode and the positive electrode has an average voltage chosen between 0.1 and 50 volts, and more especially between 0.5 and 20 volts, so that the average current density generated between the said electrodes has a value of between 0.05 and 0.25 mA/cm² and more particularly between 0.05 and 0.2 mA/cm².

12. Device according to claim 1, wherein the aqueous medium holding the active principle of the anionic oligosaccharide type and/or the aqueous medium constituting the other electrolyte hold agents which can promote the transcutaneous passage of the active principle, for example vasodilators and/or amphiphilic agents such as, in particular, compounds of the alcohol type or of the ester type.

13. Device according to claim 1, wherein the active principle of the anionic oligosaccharide type present in the reservoir element associated with the negative electrode is chosen from the alkali metal or alkaline-earth metal salts, in particular sodium, potassium or calcium salts, of oligosaccharides consisting of from three to eight saccharide units, of which some or all units have their OH groups at least in part replaced by functional groups such as, for example, —OSO₃⁻, —COO⁻, —NHSO₃⁻, —NH-acyl, —OPO₃⁻⁻, —OT where T represents a hydrocarbon radical and, in particular, an aliphatic or aromatic hydrocarbon radical, —OT being, in particular, an alkoxy group, and which have an ionic nature suitable for iontophoretic administration, the said oligosaccharides being more especially anionic oligosaccharides obtained by total chemical synthesis.

14. Device according to claim 13, wherein the anionic oligosaccharides are tri-,tetra-,penta- or hexasaccharides and more particularly pentasaccharides.

15. Device according to claim 1, wherein the anionic oligosaccharides consist of alternate uronic-acid and glucoseamine units, or alternate uronic-acid and glucose units, or alternatively alternate uronic-acid and galatosamine units.

16. Device according to claim 14, wherein the anionic oligosaccharide is a pentasaccharide of formula (II)

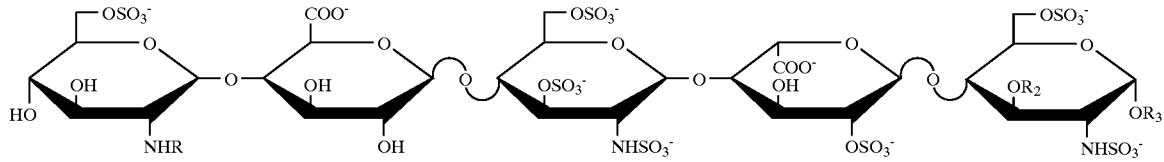

in which R is an —SO₃⁻ or acyl, in particular acetyl, group, R₁ and R₂, which are identical or different, denote H or —SO₃⁻ and R₃ represents a lower alkyl radical, in particular CH₃.

17. Device according to one of claim 1, wherein the quantity of active principle initially present in the reservoir element associated with the negative electrode represents from 1 mg to 8 mg per cm² of electrode and per mAh of current flowing per cm² of electrode.

18. Device according to claim 1, wherein the positive electrode is a reversible electrode of the same kind as the reversible negative electrode, in that the reservoir element associated with the negative electrode and the receptacle element associated with the positive electrode each hold a quantity of the active principle of the anionic oligosaccharide type which initially represents from 0.5 mg to 6 mg, and preferably from 0.5 mg to 4 mg, per cm² of electrode and per mAh of current flowing per cm² of electrode, and in that the electrical signal generator is arranged in order to reverse the polarity of the electrical signals which it applies to the electrodes in order to administer the active principle alternately from the reservoir element and from the receptacle element.

19. Use of an iontophoresis device according to claim 1 in order to administer transcutaneously to a patient an active principle of the anionic oligosaccharide type and, in particular, a synthetic anionic oligosaccharide, which active principle is chosen from the alkali metal or alkaline-earth metal salts, in particular sodium, potassium or calcium salts, of oligosaccharides which consist of from two to twelve saccharide units and, more particularly, from three to eight saccharide units, of which some or all units have their OR groups at least in part replaced by functional groups such as, for example, $-OSO_3^-$, $-COO^-$, $-NHSO_3^-$, $-NH$-acyl, $-OPO_3^{--}$, $-OT$ where T represents a hydrocarbon radical and, in particular, an aliphatic or aromatic hydrocarbon radical, $-OT$ being, in particular, an alkoxy group, and which have an ionic nature suitable for iontophoretic administration.

* * * * *

UNITED STATES PATENT AND TRADEMARK OFFICE
CERTIFICATE OF CORRECTION

PATENT NO. : 5,928,185
DATED : July 27, 1999
INVENTOR(S) : Daniel MULLER et al.

It is certified that error appears in the above-indentified patent and that said Letters Patent is hereby corrected as shown below:

Column 8, line 12, change "—$OSO_3^{31}$ " to ——$OSO_3^-$ —.

Column 8, line 26, change " —$OSO_3^{31}$ " to — —$OSO_3^-$ —.

Column 16, line 66, change "1 mA/cm$^2$" to —1 mAh/cm$^2$—.

Claim 16, line 3, in the formula (reading from left to right) change "OH", first occurrence, to —$OR_1$—.

Claim 17, line 1, delete "one of".

Signed and Sealed this

Twenty-second Day of February, 2000

Attest:

Q. TODD DICKINSON

*Attesting Officer*  *Commissioner of Patents and Trademarks*